US009309498B2

(12) United States Patent
Kim et al.

(10) Patent No.: US 9,309,498 B2
(45) Date of Patent: Apr. 12, 2016

(54) **BACTERIOPHAGE HAVING BACTERICIDAL ACTIVITY WITH RESPECT TO *ACTINOBACILLUS PLEUROPNEUMONIAE***

(75) Inventors: Ji Hoon Kim, Kyeonggi-do (KR); Tae Gyu Kim, Kyeonggi-do (KR); Seong Jun Yoon, Seoul (KR); Soo Youn Jun, Seoul (KR); Sang Hyeon Kang, Seoul (KR); Jung Min Kim, Daegu (KR); Shuk Ho Kim, Daegu (KR)

(73) Assignee: INTRON BIOTECHNOLOGY, INC., Kyeonggi-Do (KR)

( * ) Notice: Subject to any disclaimer, the term of this patent is extended or adjusted under 35 U.S.C. 154(b) by 0 days.

(21) Appl. No.: 14/349,899

(22) PCT Filed: Mar. 22, 2012

(86) PCT No.: PCT/KR2012/002045
§ 371 (c)(1),
(2), (4) Date: Aug. 12, 2014

(87) PCT Pub. No.: WO2013/051772
PCT Pub. Date: Apr. 11, 2013

(65) Prior Publication Data

US 2014/0377842 A1 Dec. 25, 2014

(30) Foreign Application Priority Data

Oct. 5, 2011 (KR) ........................ 10-2011-0101078

(51) Int. Cl.
*C12N 7/00* (2006.01)
*A61K 35/76* (2015.01)

(52) U.S. Cl.
CPC . *C12N 7/00* (2013.01); *A61K 35/76* (2013.01); *C12N 2795/00021* (2013.01); *C12N 2795/00032* (2013.01); *C12N 2795/10032* (2013.01)

(58) Field of Classification Search
None
See application file for complete search history.

(56) References Cited

U.S. PATENT DOCUMENTS

2002/0136712 A1 9/2002 Vincent et al.
2005/0260171 A1 11/2005 Ghanbari et al.
2008/0193418 A1 8/2008 Walter
2011/0052542 A1 3/2011 Shin et al.

FOREIGN PATENT DOCUMENTS

WO 2010090542 8/2010

OTHER PUBLICATIONS

Lyra et al., Mol. Gen. Genet., 1991, 228:65-69.*
Planelles et al., Analytical Biochemistry, 1999, 267:234-235.*
Rahman et al. (direct submission to GenBank, Jul. 2, 2010).*
Yeung et al., Plasmid, 1997, 37:14-153.*

* cited by examiner

*Primary Examiner* — Nicole Kinsey White
(74) *Attorney, Agent, or Firm* — Meunier Carlin & Curfman LLC

(57) ABSTRACT

The present invention relates to a bacteriophage having bactericidal activity against *Actinobacillus pleuropneumoniae*. Bacteriophage PA1Φ can infect *Actinobacillus pleuropneumoniae* and kill the same bacteria and is characterized by the genome of 34,553 by represented by SEQ ID NO: 1.

2 Claims, 3 Drawing Sheets

BACTERIOPHAGE HAVING BACTERICIDAL ACTIVITY WITH RESPECT TO *ACTINOBACILLUS PLEUROPNEUMONIAE*

TECHNICAL FIELD

The present invention relates to a bacteriophage having bactericidal activity against *Actinobacillus pleuropneumoniae.*

BACKGROUND ART

Porcine pleuropneumonia occurs worldwide and has a high rate of incidence. In Korea, it ranked as the fifth most prevalent porcine bacterial disease in 2009. This disease can affect all age groups and is tended to occur in-between seasons. Pleuropneumonia in pigs is transmitted mainly by airborne route or direct contact with an infected pig. The disease causes considerable economic losses due to increased mortality, growth retardation, and decreased feed efficiency by chronic type, etc. Recently, immune lowering viral diseases in pigs such as porcine Aujesky's disease, porcine reproductive and respiratory syndrome (PRRS), etc. are prevalent and as the scale of farming increases, the disease appears to be increasing in incidence. In addition, porcine pleuropneumonia is a highly contagious disease with sudden onset and short course, leading to mass death in swine. Therefore, there is a dire need to develop a preparation useful in prevention and treatment of porcine pleuropneumonia.

The causative agent of porcine pleuropneumonia is *Actinobacillus pleuropneumoniae*. The pathogens of this bacterium are known as polysaccharides, lipopolysaccharide, hemolysin, enterotoxin, IgA protease, bacterial outer membrane protein, etc. Sixteen serotypes are reported and twelve have been described. Serotypes 2 and 5 are most commonly isolated in Korea.

There exists a need to develop an appropriate alternative therapeutic agent for pleuropneumonia in pigs.

Recently, a bacteriophage is being magnified as an alternative to treat bacterial diseases. Due to the preference for eco-friendly methods, use of bacteriophage is of a higher interest than ever. A bacteriophage, or "phage", is a very tiny microorganism that infects bacteria. Bacteriophages kill bacteria by entering bacterial host cells and replicating. When enough phage offspring are produced host cells will be broken open and die. The phage offspring spill out of the cell and diffuse toward new hosts. Due to its very high specificity, the bacteriophage capable of infecting a specific bacterium is very limited in type. Namely, a specific bacteriophage can infect and kill only specific bacteria while affecting no other bacteria.

Bacteriophage was first found by British bacteriologist Twort in 1915 during his research on the phenomenon that micrococcus colony turns opaque somehow. Independently, French bacteriologist d'Hérelle discovered a microbe that decomposes *Shigella disentriae* in a filtrate of feces of a patient with dysentery and called the microbe a bacteriophage or bacteria-eater. Since then, bacteriophages against *Shigella dysenteriae, Salmonella Typhi*, and *Vibrio cholerae* were further identified.

After the discovery of bacteriophages, a great deal of faith was placed in their use due to their special ability to kill bacteria and many researches were conducted. With the advent of penicillin that was found by Flemming in 1941, antibiotics became popular and widely marketed. Hence, the study of bacteriophages was largely abandoned in the West except for some East European countries. However, limitations of conventional antibiotics due to antibiotic resistance that have been reported since 2000 have led to a resurgence of interest in bacteriophage as an alternative to antibiotics.

DISCLOSURE

Technical Problem

The inventors of the present invention confirmed that the isolated bacteriophage had bactericidal activity against *Actinobacillus pleuropneumoniae* and inhibitory activity against growth of *Actinobacillus pleuropneumoniae*. Based on the finding above, the present invention was finally completed.

Therefore, it is an objective of the invention to provide a bacteriophage useful in prevention and treatment of *Actinobacillus pleuropneumoniae* infection.

Technical Solution

The present invention provides a bacteriophage capable of infecting *Actinobacillus pleuropneumoniae* and killing the same.

The bacteriophage of the present invention is bacteriophage PA1Φ having a double-stranded DNA having a size of 34,553 bp and represented by SEQ ID NO: 1. The whole genome information of bacteriophage PA1Φ, which had been identified by the present inventors, was designated as GenBank Accession Number HM624080. The bacteriophage PA1Φ was deposited at Korean Collection for Type Cultures in the Korea Research Institute of Bioscience and Biotechnology, 111 Gwahangno, Yuseong-gu, Daejeon 305-806, Republic of Korea on Oct. 26, 2010 (Accession No. KCTC 11796BP).

As the bacteriophage PA1Φ of the invention can kill *Actinobacillus pleuropneumoniae*, it can be used in prophylaxis (prevention of infection) or treatment (management of infection) of various diseases caused by *Actinobacillus pleuropneumoniae.*

The term "treatment" used herein refers to (i) inhibition of a disease caused by *Actinobacillus pleuropneumoniae*; and (ii) alleviation of a disease caused by *Actinobacillus pleuropneumoniae.* The use of bacteriophage for the treatment of bacterial infections in farm animals has been demonstrated (see, for example, Wall, S. K., et al. (2010) Appl Environ Microbiol. 76(1):48-53; Huff, W. E., et al. (2003) Avian Dis. 47(4):1399-405; Callaway, T. R. (2010) Foodborne Pathog Dis. 8(2):261-6)

As used herein, the term "isolated" refers to material removed from its natural environment in which the material occurs. Isolated material undergoes a manmade transformation from its natural state. Isolated material encompasses isolated bacteriophage PA1Φ or particular bacterial isolates including the bacteriophage PA1Φ, isolated and cultured separately from the environment in which it was located. The isolates can be present in purified compositions that do not contain any significant amount of other bacteriophage or bacterial strains, respectively.

The invention further contemplates "variants" of the bacteriophage PAN), which are bacteriophage having minor variation(s) in the genomic sequence and polypeptides encoded thereby while retaining the same general genotypic and phenotypic characteristics as the bacteriophage PA1Φ. Variants of bacteriophage PA1Φ encompass polymorphic variants. Bacteriophage PA1Φ variants capable of performing the same or equivalent biological functions as bacteriophage PA1Φ are particularly preferred. Variant bacteriophage PA1Φ DNA sequences are capable of hybridizing to the referenced SEQ ID NO.:1 under highly stringent conditions (two single strands will hybridize when incubated in 0.1×SSC (15 mM NaCl, 1.5 mM $Na_3$-citrate-$2H_2O$; pH 7.0) at 65° C., but not at higher temperatures.

The bacteriophage PA1Φ of the invention can be used to improve or maintain animal health by preventing or treating bacterial infection. As a result of use of the bacteriophage PA1Φ, the animal may exhibit better performance as reflected by maintaining or improving one or more of the following characteristics: diet, growth, food conversion, survival, appearance, production (e.g., milk production), and/or work rate.

Advantageous Effects

The bacteriophage PA1Φ can provide specific bactericidal activity against *Actinobacillus pleuropneumoniae* without affecting other useful normal flora. Accordingly, the use of the bacteriophage PA1Φ causes little side effects. In general, use of chemical materials such as antibiotics, etc., causes harm to other normal flora, thereby resulting in various side effects such as lowered immunity, etc.

BEST MODE

Hereinafter, the present invention will be described in more detail with reference to the examples, which are set forth to illustrate, but are not intended to limit the present invention.

Example 1

Screening of Bacteriophages for Ability to Kill *Actinobacillus pleuropneumoniae*

In order to select a bacteriophage capable of killing *Actinobacillus pleuropneumoniae*, about 300 types of bacteriophages which had been previously isolated by the present inventors and available at hand, were tested with regard to activity to kill *Actinobacillus pleuropneumoniae*. These bacteriophages had been collected from pigsty environments or animal tissues.

The activity to kill *Actinobacillus pleuropneumoniae* was evaluated by spot testing. The assay was performed as follows: *Actinobacillus pleuropneumoniae* (ATCC 27089) in a 1:1000 dilution was inoculated on a TSB (tryptic soy broth) medium (casein digest, 17 g/L; soybean digest, 3 g/L; dextrose, 2.5 g/L; NaCl, 5 g/L; dipotassium phosphate, 2.5 g/L) supplemented with 2 μg/ml of NAD (nicotineamide adenine dinucleotide) and then shaking-culture was performed at 37° C. overnight to obtain a culture solution. Three ml of the culture solution ($OD_{600}$ is 2.0) was spread on a TSA (tryptic soy agar) plate (casein digest, 15 g/L; soybean digest, 5 g/L; NaCl, 5 g/L; agar, 15 g/L) supplemented with 2 μg/ml of NAD and then the plate was allowed stand on a clean bench for about 30 minutes so as to dry the liquid spread on the medium. Ten μl at a time of the previously prepared bacteriophage suspension was dropped onto the plate inoculated with *Actinobacillus pleuropneumoniae* at a time and the plate was allowed to stand for 30 minutes again so as to be dried.

The bacteriophage suspension used in the present testing was prepared by a conventional method (Korean Patent No. 10-0781669), said method is hereby incorporated by reference. The procedure of the method is explained in brief as follows: the bacteriophage culture solution which had been prepared using an appropriate host bacterium was centrifuged at a speed of 8,000 rpm for 20 minutes so as to harvest a supernatant. The supernatant thus harvested was filtrated with a 0.45 μm filter and PEG and NaCl were added to 100 ml of the filtrate so as to make 10% polyethylene glycol (PEG) 8000/0.5 M NaCl. The mixture thus made was allowed to stand for 2-3 hours at room temperature, followed by centrifugation at a speed of 8,000 rpm for 30 minutes to obtain a bacteriophage precipitate. The resultant precipitate was resuspended in 5 ml of a buffer (10 mM Tris-HCl, 10 mM $MgSO_4$, 0.1% gelatin, pH 7.5). The resultant suspension was used as the bacteriophage suspension.

The bacteriophage suspension was spotted onto the plate, followed by static culture at 37° C. for a day. The area covered by the spot was checked for clearing. Clearing of the spot area presumes the *Actinobacillus pleuropneumoniae* killing activity of the bacteriophage tested.

Figure 1:
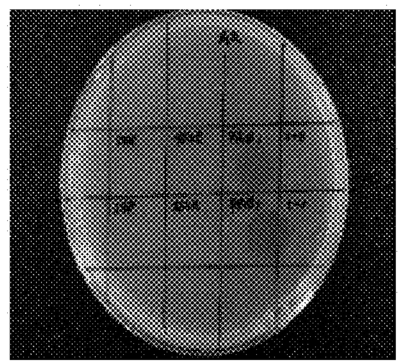
FIG. 1 is the result of bacteriophage screening showing a clear zone formed on the area spotted by bacteriophage PA1Φ.

Based on the results of the assays conducted on about 300 types of bacteriophages, a bacteriophage could be screened for clearing on the spot, i.e., activity of killing *Actinobacillus pleuropneumoniae*. The bacteriophage showing activity of killing *Actinobacillus pleuropneumoniae* was bacteriophage PA1Φ. FIG. 1 shows the clearing on the spot area by bacteriophage PA1Φ, observed during the screening procedures. Bacteriophage PA1Φ has been previously deposited by the present inventors at Korean Collection for Type Cultures in the Korea Research Institute of Bioscience and Biotechnology (Accession No. KCTC 11796BP). The entire sequence information of the bacteriophage PA1Φ was also identified as GenBank Accession Number HM624080 by the present inventors.

Bacteriophage PA1Φ needs a suitable host strain such as *Pseudomonas aeruginosa*. The results of the present working example confirmed that bacteriophage PA1Φ can infect *Actinobacillus pleuropneumoniae* and kill the same.

Example 2

Investigation of Bacteriophage PA1Φ Killing Activity Against *Actinobacillus pleuropneumoniae*

Figure 2:
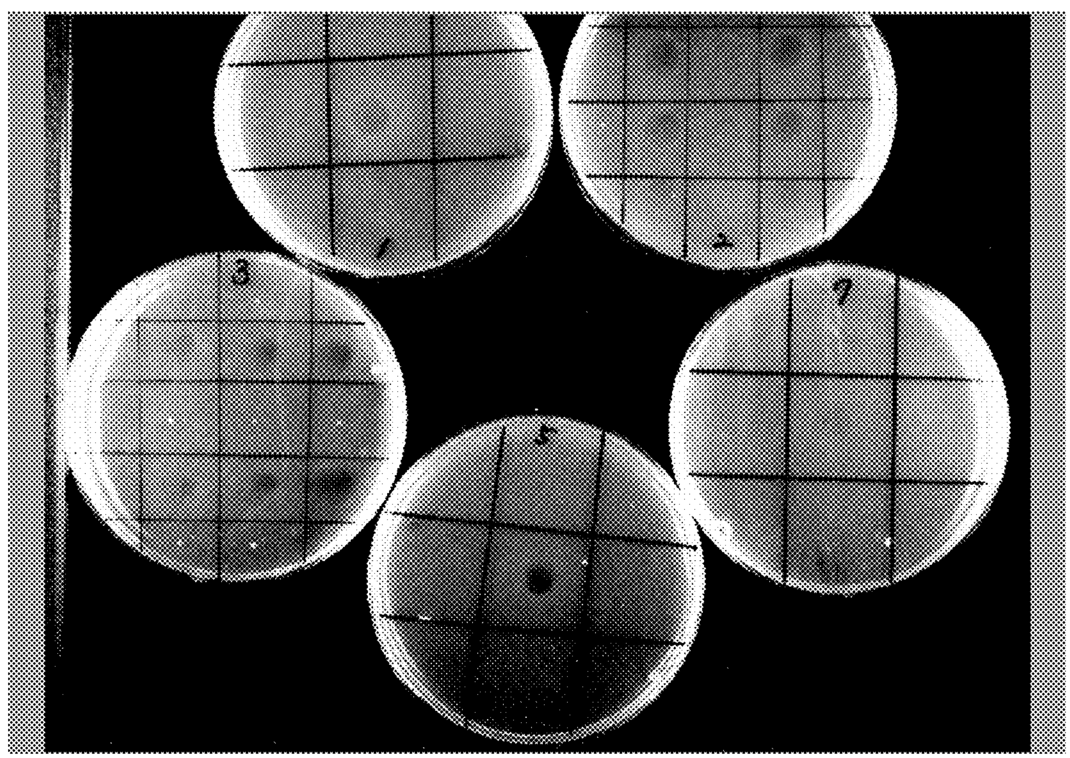
FIG. 2 is the result of the assay of bacteriophage PA1Φ for activity of killing various *Actinobacillus pleuropneumoniae* strains.

In order to reconfirm killing activity of bacteriophage PA1Φ against *Actinobacillus pleuropneumoniae*, standard and isolated strains of *Actinobacillus pleuropneumoniae* were tested for bacterial lysis by spot testing. The spot testing was performed in the same fashion as described in EXAMPLE 1. The *Actinobacillus pleuropneumoniae* strains used were ATCC 27089, ATCC 27090, ATCC 33377, BA01849, and BA01850. ATCC 27089, ATCC 27090, and ATCC 33377 are standard strains, and BA01849 and BA01850, which were provided by National Veterinary Research & Quarantine Service, are isolated strains. As shown in FIG. 2 illustrating the result from this assay, bacteriophage PA1Φ had killing activity against various *Actinobacillus pleuropneumoniae* strains.

Consideration of the foregoing results indicated that bacteriophage PA1Φ can be used for prevention and treatment of *Actinobacillus pleuropneumoniae* infection.

Example 3

Investigation of Inhibitory Activity of Bacteriophage PA1Φ Against Growth of *Actinobacillus pleuropneumoniae*

Figure 3:
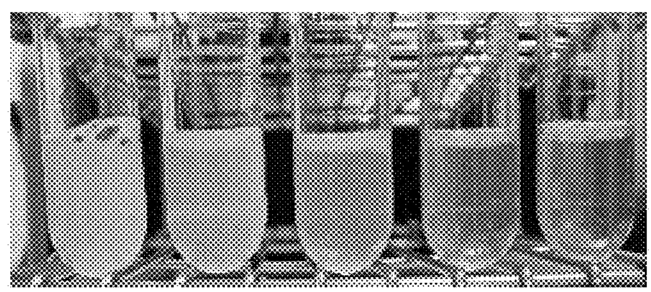
FIG. 3 is the result showing growth inhibition of *Actinobacillus pleuropneumoniae* when the bacteriophage PA1Φ ($2\times10^8$ pfu/ml) was added in an amounts of 0, 0.125, 0.25, 0.5, and 1 ml to the tubes (in order from the left).

It was examined whether the presence of bacteriophage PA1Φ can inhibit growth of *Actinobacillus pleuropneumoniae*. To a TSB medium comprising 2 μg/ml, NAD was inoculated in a 1:1000 ratio and shaking culture was then performed overnight. The culture solution thus prepared was diluted with a TSB medium supplemented with a 2 μg/ml of NAD such that $OD_{600}$ is adjusted to 1.0. To the dilution was added the bacteriophage PA1Φ suspension ($2\times10^8$ pfu/ml) in an amount of 0, 0.125, 0.25, 0.5, and 1 ml, respectively, followed by addition of a TSB medium supplemented with 2 ug/ml NAD such that the final volume became 2 ml. The culture solution thus prepared was shaking-cultured at 37° C. overnight. The result of the shaking-culture was shown in FIG. 3. As seen from said result, as the amount of bacteriophage PA1Φ increased, the growth of *Actinobacillus pleuropneumoniae* was slowed.

The results described above confirmed that bacteriophage PA1Φ can inhibit growth of *Actinobacillus pleuropneumoniae*, and thus, it can be used for preventing infection by the same bacteria.

While the specific embodiments of the present invention have been described above, it is apparent to those skilled in the art that they are only preferred embodiments and the scope of the invention is not limited thereto. Thus, the scope of the present invention is substantially defined by the claims attached hereto and equivalents thereof.

[Number of Accession]

Name of Accession Institute: Korean Agricultural Culture Collection

Number of Accession: KCTC 11796BP

Date of Accession: Oct. 26, 2010

The invention claimed is:

1. A method for treating *Actinobacillus pleuropneumoniae* infections, comprising administering an isolated bacteriophage PA1Φ deposited under Korean Collection for Type Cultures Accession No. KCTC 11796BP to an animal subject, wherein the said bacteriophage PA1Φ has killing activity against *Actinobacillus pleuropneumoniae* strains.

2. The method according to claim 1, wherein the bacteriophage PA1Φ has a genome comprising SEQ ID NO: 1.

* * * * *

SEQUENCE LISTING

```
<160> NUMBER OF SEQ ID NOS: 1

<210> SEQ ID NO 1
<211> LENGTH: 34553
<212> TYPE: DNA
<213> ORGANISM: Bacteriophage PA1

<400> SEQUENCE: 1

tccgaaagct ggcagaaagg gaaggctgga agaagcagaa gcactccggg cgcggtggtg      60

gatatgagta ccacgtttcg gccctgccga aagaaacccg cgccgcgctg ctgaacgccg     120

ccctgggcga ggtggccacc aaggtggtcc gccaggagac gcaactggcc ctggtcgaaa     180

ccaaccgcca gcagctggtc gccgatgccc gccagggggt gctgcacgcc ctggacctga     240

tgatggcccg caccggctac agccggaaac gctccatcac cctgatgctg gacatggcgc     300

gcctcggcca ggtcgagccg caactgctcg ccatgctcaa gatggcccgc gatcctcgcg     360

gccgcccgag cgcggatggc ctgccgagcg tgcgcagcct ggagcgcttc ctggaccaag     420

ccgagcgtgg cgccctggtg ccgaaggtcc gccgcccgga catgagcgtt cccgactggg     480

cgccggcatt catgacgatc taccaggggc cggagaagcg cagcgcccgc gctgcccatg     540

cactgctgga gaagcactgg caggggcaaa tgcccagcct ggaccaggtc tatgcgttcc     600

tgcgcaaggt cggcaacgtc agccgcgagg tcgggcgcat gggtgagcat gaaatcaagg     660

cgctgcgccc gttcattcgc cgcgacttca ccaagctgct cccgaccgac gtctattcat     720

gcgacggcca cacgttcgac gccgaggtcc agcacccgat gcacggccgg cccttccggc     780

cggaaatcac caccatcatc gacatccgta cccgtcgaat tccgggatgg tccaccggct     840

tggccgagtc ggccctggtg gtggtcgatg ccctgcgtga cgcctgcacc aagggcggca     900

ttccggccat cttctacgtg gacaacggct cgggctacat caaccacatg atgcgcgacg     960

aggcggtcgg ccttatgggc cgcctgggca tcgatatgaa gaacagcctg ccctacaaca    1020

gccaggcgcg gggcgtgatt gagcgcgtcc accagagcct gtggattcgg gccgccaagg    1080

aactgcccgg ctacatcggc gccgacatgg accgccaggc caagctggcc accttcaagc    1140

tgactcgccg ggccattgcc aagggcggca ccatgccgct gatgtcttgg gaatcttttg    1200

tcgcgttctg cgagcaacag attgccgagt acaacgaccg gccgcacagc agcttgccgc    1260

gcatcgttga cccgaacacc ggccgtcgcc ggcacatgac ccccaacgaa gcgtgggcgc    1320

tccacgaagc cgatggcttc cgcccgatgc gggtcaccga cgacgaggcc cggccgctgt    1380
```

```
tccggcccca ggtgctgcgc accgtccgcc gctgcgaact ggagttcatc ggcaaccgct   1440
acttcgcccg cgagctggag gaattccacg gcgaccaggt ggccgtgggc tacgacatcc   1500
acgacgccag caaggtgtgg gtctacgacg gcgagggccg cttcctttgc accgcagagc   1560
tgaacggcaa cagccgcgac tacatgccgg cttcgtatgt cgagcgtgcc cgcgagaaac   1620
gcgcagaggc ccgcgagaag cgcgccctgg ctcacctcga cgagattcgc gccgagcgtg   1680
acggcgggta tgccctggaa atggatgcgc cgctgtccat ccccggcctc ggcacgatca   1740
cccctgagca actccggtcg cgcagcgccg cgaccctcga aatgcaggcc gagcggatcg   1800
acgaaccgcg cccggccgca gccaccgccc aagccaccac cgcccaggtc ttcaccctgc   1860
cgaccgctcc cgcccagcgc taccggcagt ggtgcgagct ggccgagcgg cagcgctccg   1920
gccaacccat cgagccggac gccgcccagt ggttcgaggt ttaccccaaa tccaaagaat   1980
tcgccgccca gcagcggcaa gcatgaaagg agctgtattc atgaccaccc cgaaaaccac   2040
ccaactggcc agcggcatgg ccgacatcgc caacatcgcc ctttgcgata tcgccctgga   2100
gaaagcgctg tcgcgtacct ccaccttgcc cggcctggtc tgcttctacg gcccgtccgg   2160
cttcggcaaa tccgtttcgg ccgcctgggt cgccaatcgc cgccgcgcct actacgtcca   2220
ggccaaaagc gtctggaccc gcaagcacac gctgaagtcg atcctgggtg aaatgggcat   2280
caagccggcc gggaccatcc cggaaatggc cgaccagatc gccgaggaac tggccgccag   2340
cggccgcccg ctgatcatcg acgaaatgga ccacctggtc gccgctggcc aggtcgagct   2400
gattcgtgat ctgtacgagt ccagccaagc ctccatcttg ctgatcggcg aggaaatgct   2460
gccgaccaag ctcaagaagt acgaacgctt ccatggccgc gttctcagct gggttccggc   2520
ccagccagtg tccctggagg acgcccgcaa cctggcgccg gtctacagcc ccggagtggc   2580
tatcgctgac gatttgctcg cgcacctggt gaagaagtcc ctgggctctg tccgtcgcgt   2640
cgcggtgaac ctggagcagt tggccgaggc cgccaccgtt cagggccggc gcgagctgga   2700
actggccgac ctccagcgcc tgaacctgga gctgtatacc ggcgcggccc cgagcccgag   2760
gacttcgaag tgagcctcgg caagaacccg gcccacctgt ctatggtcgg gggcaagagc   2820
ccccgccagc agatgtggga agtcatccgg gccaaccgcg aagagttcac cgtctaccgc   2880
gtggcgcgcc gctccaacca gcacgacaag accgtcgaga agtatgtcgc ctgcctgcgc   2940
ctgggcggct acgtcgaggc gatccgtgga ttcaagcgcg gcgaagaagt cgtttttccaa   3000
ctggtccgcg acaacggcgt cgaggcaccg aacctgaacg ccgatggcaa gccatcccag   3060
cagggctaca ccaccgaggc ggtctggcgg acgttgcgaa tcctcggccc atcgaccccg   3120
gaacagatcg ccgcatcggt ggcggcctcg ggcacgcccg tgtcgcccag caccgttcag   3180
cgctacttca tcgacctcca aaacgccgga tacctgaccc gcaacggccg ccactacgcc   3240
ctcaagccgg gccgctacac cggtccacgg ccgcccatcg tccagcgcga gacgcgccgc   3300
caggtctacg acccgaacct ggaccaggtc atgtggagtt cgcacggcga gtaccagcac   3360
aaccggagcc gttccaagaa atcagaacag gaggtgccgc catgcgccga gcactgatcc   3420
ccatcggcat cttcctggcc ctcggcctgc tgctggtcct ggccggtgat gccctgatgc   3480
tcggccgccg cctcattgcc tggcaatggg ggtgctaatg gaccgcgcaa tcgatctgtc   3540
ggcctggggc gagcgcccgc ccgtcttcgt ccaactgctg gccgctgagg tggcccgcag   3600
cagccagacg aaagccggcg aggcaatcgg catgagccgt tcgaccgtca gcaccatcct   3660
cgccaaccgc tacccgtcgc cctcgacgat ccgcgtcgag cgtcgtgtcc tggccgcgct   3720
gagccgcatt gagtgcccgg ccctgggcga ggcggtgacc tcggtcgagt gtagcgagta   3780
```

-continued

```
cctccagcgg ccggcgccgc tgaacaaccc cgtcgcgatg cgctgctgga aagcgtgccg   3840
cgcctgtcca cgcaacccgc ataccgcccc catgaaacga gaggaacaag gccatgagaa   3900
ccgcattgcc cttgaaagtc ttgacgcctg acttggccct gagcctgcgc accttcaacg   3960
atgccgcccg gttgctccag cgcatggggg ttcgccttca tcgcctggag ccgacagagg   4020
ggcgcgtgac catcgccgca gatgacgccc gccagctcct ggagaagggg ctcctgctgg   4080
gtttccagcg cgaggcctcg gccggcagca cccgttacat cacccgcttc cagggcatca   4140
ccctggcctg gagcgaaccg atcagctacc gcgacttcgc cggcagcaaa cccgtaattc   4200
actgaacagg agaacgccaa catggcatcg aagaaacgtc tgaaatccgc tgccgccgtc   4260
tacgtcccgc agacccgcga gcaggtcatc agcgatatca agaacatcgg cgacctccag   4320
cgcgagctgg cccgtctgga aaccgcaatg aacgatgaaa tcggccagat caccgagcgc   4380
tattcggagc cggccgaaga cctgaagaag cgcctggcgg tcctccaggg cggagtccag   4440
tcctggtgcg aggccaaccg tgccgagctg accgacaaca acaaggtcaa gtacgcgaac   4500
ctcacgaccg gcgaggtcca gtggcgcatc cgtccccgt ccgtgactgt gcgcggcgcc   4560
gatgcggtcc tggagctact gcgcagcaag ggctaatcc gcttcatccg caccaaggaa   4620
gaggtgaaca aggaagcgat cctcaacgaa cccgaggccg tccaggggct gccggggctg   4680
accctgaaca cgggcatcga agacttcgcc atcgtgcctt tcgaagcgga ggtgcagtga   4740
catggccgag gaaatcagca tcgacaccat catgtcgcag gcccaggtat tcgccagtgc   4800
ttgggcgctg gtcgggggca cattcgacga cggccacgcc atcgagaacg ctgaggaagc   4860
caaggctgaa ctgcgcgaaa tgctggagga cttctgttcg aacactgacc tcctgcgcgt   4920
ggctgagctg ctcacctctt ggcaccagaa cgggatgggc aagattgatc aggcgctgaa   4980
tgcgccggat acggccgagg ttcggattgg ctcggccagg ctcactggtt cccaagccat   5040
cggcttccga atcggcctac gagtggcccg ccagtggctt ggcacactcc cgctatcgct   5100
caccaaacag gaggtgtgac atggcccgca accgcgcgca acagctgtgc atcgtcacct   5160
tggactatca gcgcttcctg ttaccccagg ctgatgcact caagctgata gacatcatga   5220
gtcgagccgc agaggttcag gccgactacg cctctggagc tgggttcaag tacaccgtcg   5280
gcgaagtgcc ggaagtcgag ttgacgatag tacgccccag tcaattggtc atgccgcagg   5340
ccgagccggc cccagctaca ccacgcgctc gccggaagtc tccggcccag gtcacgcacg   5400
atgccattcg gctgctggag ggctctgat catgaccaag acgttcgcca tgtgccgcat   5460
cgacggcctg atcgagctgc gggaggaaca cccaggcgag ggctacttcg cccttgccgt   5520
gggcgacttg gccagcgtgc gggcggcggt ctttgcaacc gctgagccgc accaggtcgg   5580
caagaaagtc gcccggcgcg tgccgggtgt gagccccgac gccaccgacc gcgaaaacct   5640
gggctccatc gcccggtaca tccagaccct gggccagcag gatcggccgg gcttccgtgc   5700
gctgggggtg tgaaatgcag cagtccaacc ccttcaatca ccccggacag agctacggcg   5760
ccgtagacgt cgatagccga ctccgcgccg ttgccggctt cgacctggag caatgccgcg   5820
ccgcgctcgc ggtcaccggc ctccagaaga tcgtcgagca gaaaattcgc acccgcatcc   5880
gccagctgga aaagcaggca tccgcacaga aggaggcata accatggccg tatacaccat   5940
caccctcagc gacaccgagc gcggaataga tttctccatg caaggcccgc cgctgcacga   6000
ctccgaagca tcgaaggtcg cctatgccct tatgcaagcg acgatgtccc tcggccagga   6060
actcgcaaag cagaacggag ctggtaacgg cgtttcctgc gcctgcgacg agtgcctggc   6120
```

-continued

```
gcgccgcgct cgcggcgaag aaccgcagca ggaaatccac tacaccaagg ccaagaaccg   6180
caccgtccat tgagcgaaac cgccccggcc ttgccgggac ggtctgccgg acgtggtggt   6240
ccggtactga tgagcagcca cccatgacga acgaaaccaa gacagaccgc cagcggcgcc   6300
tggcgcggga acgccaacgg gcgaagcgcg agcgcgatgc cctgcgtcgc gctgcgctgg   6360
gcggccgccg cttcaacatg gacatgtacc agggaacggc tgatgcactc gatctgatct   6420
gcgcggccgg tggcttcgcc gagccggccg aggcggtcac cttgctccta cacaacgttg   6480
ccgaaattgc agagcgtgac gcgtcacgtt ttgccgagtt gatccaaaag agaagccatc   6540
cagggaggac caagcgatga gcctacgcgc cgtcaacctc gcaaaaatcc acatcgccaa   6600
ggcccagctg ggcatggacg atgacaccta tcgcgcattg ctggctcgcg tcgcgggcgt   6660
gcgctcggcc aaggacttag ggccgcgcca gatcgaccac gtactggtcg aactccagcg   6720
cctgggctgg aaaccgaaga gcaaccggca gggccgggcg acgccaaaag tgccgcaaaa   6780
ccggcaaacc gtgctgcgca aaatcaccgc gctcctggcc agcgcccatc gcccctggag   6840
ctacgccgac cacatggccc ggcgcatgtt ccaggtcgag cgggtcgagt ggctggacga   6900
cagccagctc taccggctga tgcaggcgct tatcatcgat aggagccgcc atggccaggt   6960
ctgaggtgga tcttcgggag gtccaggaca tgctgccgga taccgtccgc gacatggccg   7020
gacgcatagg actgccggcc accctggtgg tggtcgagca gctcggcgga acgtcctggc   7080
ggatagccga gggccgggcg cggaggggcg aagcgcgccg ggctgcgctg gccgagctgg   7140
tgggcagcga catcgaggag cagctccaca cgcactatcg ggcgaagaa atttacgtgg   7200
cccgctgcca caaggcgctg gtacggtggc gcgatctgga gatcgtcgag cgcttcgaac   7260
agggcttgcg tgatgggcaa accgcccgta gcctgctcag cgatctagcc cgccagtaca   7320
acctgtccga ccgctggata tgggagattg tcaaccggcc gagcgagccg gcaccgcagc   7380
aatccaccct gttccactaa gccggggcgc aacgccccgg ccggcgtctc cgcgccgatc   7440
ctatctcagc cgttgaaccc cttccgctaa tcccgcgtcg cactcgccgc cacgatggcg   7500
gcatgagcac atctagcccc tcaacgtctc tacgcagccc ccgcgactac gccgccgcca   7560
tcctggccga gcccagccgc gagcgtcgta acgctctgct ggcagcctgc ccggccaact   7620
ggcagccgct tgttcgggcg cacgtcgagg atgccttcgc gaaggtcaag gcgtatcgcc   7680
agatgatgga caaccgcgcc gagtcgatcc ggcgcggccc gcctcctgct ccccgcgtca   7740
ccgacaccga tttccgcata tccaactaca ccaagtccgc cccggaggta ggcaatgcgc   7800
acctatccgc aattcgggca gcgctcgcaa cggaagcacc aaatgcctga tcccgcatcc   7860
acctcggccg gcagcgccgc gctgctgaaa atgttcggca tccacataag cgcgggcgcc   7920
ctggctgccg ccctgggctt ccttgtcctg tggccccgaa caatgaaaga ggggttcgcc   7980
cggctgttct gcaccatcgt cgcgtccagc gtcttcggcc caatcctggt ggtttacctg   8040
cactccaaac gccccgagtt gttcgagtcg gcccatgtgg tggccgggct ctaccagctg   8100
gagccagcgg tcggcctgct gttcgtttcc gctccgctcc tggtgattgc cggtctgcct   8160
gcctggtggc tgatcggtgc ggccctgcgc ctgtttgagc gggacggcga ttcatggctg   8220
ggcgcgttcg cccagtgggt aaaacgcaaa ctggagaaca actgatggcc cttcaacctc   8280
gcggcatccg caacaacaac cccggcaaca tcgtttggtc ggcacgcaac aactggcagg   8340
gccagctccc gcacaacccg aagatcgagc cccgattcgc ccgcttcgac accgcgcata   8400
acggcatccg cgccctggca aagctgctgc tgaactatcg caaggtctac ggcctgcgca   8460
ccgtcgaatc gttgatcgca cgctgggcgc cgtccaacga gaacgacacc cgcgcatatg   8520
```

```
ccacggccgt ggcccgagcc atgggggttc cgccgcaggc cggcctgcac atggaccagg   8580
acaccctggc cgccctggtg accgcgatca ttcggcacga aaacgggcag cagccctaca   8640
gcgccgagca gatcgcccag gctgtgcggg aggtgctgtg atgcagcgcc ccagcggaat   8700
cagcctcagc gatctgttcg cgatctgccg tgaagacccg gccaaccgat ggctctggat   8760
acgcctctat ctccgcgacc tgctggcccg cgtcgtgatt ctggtcttca tggcaattgg   8820
tgccgcaggc ctcgcctatg gcctgggcgg ggcgttcgcc tacggcttca tgcagaccgt   8880
tgcgtcctac caggtccagc tcagcgtcga gaaatcgcca tgacctggcg cgtcggcctg   8940
gttgtctttg tgctcctggt gatggtctgg acggccggct ggtggggcgg tcgcgaggcc   9000
ggtctggccg atgggcgcgc cgcctgcgct gacgcacaga cccgcgcata tcgcgacgtc   9060
ctggagcaat cggcggcaca actgaagacg gtccaggaca ccagcgcggc tcttttccag   9120
cgcctggccc agcgggccga cagcgaccaa caaactactc gggagcttcg ccatgccctg   9180
gccgaaaccg ctgctgatcg cgctgcctgc cgctttcctg ctggcgtcat gcagcagctc   9240
gaaaccgccc gtcaacgtgc cgcccaggcc actaccagcg gccttggctc aaccgtgcca   9300
gaccccggtg gcggtgactg atgacagccc cgatgccgcc gcaattgccc ttaaacaact   9360
ctacgaccaa tacggcgctt gcgccggcct gcactgggac accgtgcggc accttcaaaa   9420
ggactgatcc gatgaccgaa aagaaagcct ctcctgagtt cgaactgctg caacgcatcg   9480
acggccgcct ggagcgcttc gaagaccgat tcccgcagat cgaacgcaag gccgtgctgt   9540
acggctcggc ggccggcgcg ctggcgggtg gcctggttgc ctgcggcctg ctcgcggcgc   9600
gtatcaagct cggtatctga ggtagtcgat ggcgcacccg aaggaaaccc gcgacgccct   9660
gcgccgcgcc tacgtcctcg accgccagtc cctggaggtc gcggccgcca tgttcggcgt   9720
ctcctacggc accgcccgcc gctggaaaca gcaggcggaa gccgaggggg acgactggga   9780
caaggcacaa tcggcgcagt tgctggccgg tggtgggctg gaggacgtgg cgcgccaggt   9840
gctggccggc ctggtgaccc agttccaggc caccatggag gcgatccagg tggacagcgc   9900
gatcacgcca gcggtcaagg tgcagatgct cgccagcctg gccgacgcct acaacaagtc   9960
gatcagcgca tcgaagcggg tactaccgga aacctccagc ctggccaccg caatggaagt  10020
catccagcgc ctcgcggcct tcatccgtga acagttcccg cagcacgtcc aggccttcgc  10080
cgagattctg gagccgttcg gggaagtaat cgctaagggg ctgaaatgaa caccgaggaa  10140
aaagagttcc tacgggaact atccgccatg gcgcagcagc tgcgccgcga catcgaggcg  10200
caacaggtcg gcctcgatag ctccccggaa gctcgggctg agcggcgccg tcgcgtactg  10260
gtagatcgcg atttcgagtt cttcgcgtat acctacttcc cgcaccacat ccggccgcct  10320
gcctcgttgt tccatgcgca tttcttcaag cgctttcccc agctcatcag cacctccagc  10380
ggcctcaagg aatggtgggt agctccgcgt ggcgaggcga agtcctcact gctgaccaag  10440
gtcgggccgt gctatgtcgt tgtccagggg ctgctccagc gaccggagat tcgggccgaa  10500
ctgggcatga ccggcccggc gccgtacttc gtcgactaca tcacgctcct aggcgccgaa  10560
acgcgcttgc ccaccaagct cctggaagta gtcaagaccg agctactggt aaacgcctcc  10620
ctgtccctgg acttccccga agtctgcggc aagggaagcg tctggaagat cggcgagttt  10680
gtttccctct ccggggtcaa gctggaggcc ttcggcgctg aacaggcgat ccggggcaca  10740
ttccacggcg cgagccgtcc caagctgctc ctgggcgatg acctgatcac cgacaaagag  10800
gccaagtccc cgaccgagcg caacaaccgc tgggactggc tggaaaaggc tatcgactac  10860
```

```
ctcggcccac cggatggctc cgtcaaatat ctaggcgtgg gcacagtgct gaataaggac  10920
gatccgatca gccgagccaa acgcacggtc gggcacctgg tccaccactt ccgcgctatc  10980
gagacgttcc ccgcccacat ggacctatgg gcacattgcg aagaggtgat gctcaacgac  11040
gacaagcctg tgatggagca atacgccgag cgcggtagcg tcgcgcccga tagcgctctg  11100
ccgtcgtttc agttctacca ggataaccgc gagcagatgg aactgggggc cgtcaccagt  11160
tggccaggtg tccggtcgct ctactggctg atgcgtcagc gggcgaagaa caaagccgcg  11220
ttcgcgaccg agctgcaagg cgacccgcga tccgatgaag acaagacgtt taccaacccg  11280
cgcttttggg tcatgcgctc cggccgttgg cagatgtttg gcgcctgcga cccctctgtc  11340
ggggcgagcg cacagtccga cccgtcggca atcatcgtgg ggggctggga caccgagaaa  11400
caggtactca acgtcataga ggcggccatc aagcggcgcg tcccctcgaa actggaatcg  11460
gacttgatca aggcgcaaag ggagtaccag atgcgcgcta tcggtttcga gaacaacggg  11520
gcattcgaaa tccagcggca gaacatcgcc aaggctgcgc tgatgcagcg cgtagcgctc  11580
cctctggtcg gtgttaccag catggcggac cagtccgttc gaatcgatgc catggagccg  11640
ttcatcaacg acgcatttgc gccacggatt ctgttttcac ctggattggt cgccctgctc  11700
gacgagctgg acagctggcc agaaccgcag accgggcacc actacgacgg cctttgcgcc  11760
ctgtcgatcc tctggatgat cgctagcacc cgcgctggtt cctatgaatt caccccggtg  11820
cctggccgtc gcagctctgc ggattccagt gagttcaaag actcttttga cataggtggc  11880
cgcatgggcg gcgactggta ggagacgcaa cgatggccac catcgtggat atttacggca  11940
acccccctgcg aacccagcag ctgcgcaagc agcagaccgc gcacctgacg ggactggcca  12000
aagagttcgc aaaccacccg gccaaggggc tgaccccagc caagttggct cgcatcttga  12060
tcgaggccga gcagggtcaa ctccaggctc aggccgagct gttcatggac atggaggaac  12120
gcgacgccca cctattcgca gaaatgagca agcgcaagcg cgctgtcctc ggcctggact  12180
ggaccatcga gccgccacgc aacgcctcgg ccgcagagaa ggccgacgcg gagtatctcc  12240
acgagctgct gctcgacctg gagggcattg aagacctcat gctcgattgc atggatggcg  12300
tcggccacgg ctatagcgct atcgagctgg actggtccct ccagggacgg gagtggttgc  12360
cgcaggcctt cgaccaccgg ccgcaaagct ggtttcaact gaacccggac gaccaggacg  12420
agctgcgctt gcgcgataac agcatcgcgg gcgaggtact ccagccgttc ggctggatca  12480
tgcacaagcc gcgttcgcgc tcgggatacg tggcgcgtag cgggctgttc cgcgtgctgg  12540
cctggccgta cctgttcaag cactactcca cggccgacct ggcggaaatg ctcgaaatct  12600
acggtctgcc gatccggctc gggaagtacc cgcccggcac gcccgacgaa gagaaggtga  12660
ccctgctgcg ggccgtgacc ggcctcggcc atgccgcagc aggcatcatc cccgagagta  12720
tgtccatcga gttccaggaa gcgtcgaaag gctcggccga gccgttcatg gccatgatgc  12780
gctggtgcga tgactcaatg tcgaaggcca tcctgggcgg cacgctcacc agccagacca  12840
gcgagtcggg cggtggtgcc tatgccctgg ggcaggtcca taacgaggtg cgccatgacc  12900
ttctggcggc ggatgcccga cagctcgccg ccacgctgag ccgagaccta ctctggcccc  12960
tcctggtcct caaccgctcc ggcaacctcg acgcacgccg cgcccccgc ctggtgttcg  13020
acctcaagga ccgggccgac ctggccgcca tggcaacgtc attaccgccc ctggtcaagt  13080
tgggcgtcca ggttccggtc aactgggtcc aggagcaact gggaatcccg ctgccggcca  13140
agggcgaggc agtcctggtc gatcaggccg gcgcaggcat cgcccaactg agccggcgcc  13200
ctggtcctcg cgtcgctgcg ctggcccagg tgattggacc acgctaccgc gatcaggaag  13260
```

-continued

```
cgctggacca ggtgctggcc agcctgccag cccaggacat gcaaaaccag gccgatagcc  13320
tggtcgcgcc gctcctggat gtgatcagcc gtggaggtag cgaggcagag ctgctcggcg  13380
cgctggccga ggcattcccg gatatggacg atagcgccct ggcggatgcc ctccatcggt  13440
tgctgttcgt ggccgacacc tggggccggc tcaatggcac gttggatcgg atcgactgat  13500
ggcaacgcca accgaggccg atctgcgggc catcttcgcc atgcggccgg aggccgccat  13560
tgagtacctg gagcgcaagg gattcgccat tacctggaac tggcacgatg ttgacgcggc  13620
cacccatgcc cgagcgctga cggtggccaa ggcggcacgc ctggacgtgc tccaggacat  13680
ccgcgacgcc ctggtcgata acctggagcg tggcggaacg ctgcgcgact tccagcgcaa  13740
cctgcggccg atcctggagg ccaagggctg gtgggggcgt cagatagtgg ttgcgccgga  13800
cggcggggcc gaggtcgccc agctcggcag cccgcgccgg ctggaaacga tctaccagac  13860
caacgtgcag tcggcctaca tggccgggcg ctatgccgcc gcatacgagg ccagggaaac  13920
tcacccttac tggatgtatg tggccgtcat ggacagcgtc acccggccca gccatgcggc  13980
gctacatggc aaggtgttcc gctgggacga cccgatctgg cagcacatca tgccgccgaa  14040
tggctacaac tgccggtgcc gaatcgttcc gttgacggcg gccgctgtgc gtcgccgtgg  14100
tctgacggtc gaatccagcg tcggcaagac cggccaggtg accgtcgaga cgggcgtaga  14160
caagcggacg gggagattc gggagcagac cttgaccacc ctggagacga ccgaccgggc  14220
cggtcggaag atccaatttc gccccgatgc cgggttcgac ggcagcccga tacagagcgc  14280
cctgatggac caggtgctgt acaacaaggc cgagcgcacc ctgggagcgc ctgccgccct  14340
cggcgaggtc caggacgtgc tcctggaccc ggtacgccag cgcgcttggc aagcgtttgt  14400
ggaccgctcc acgtcgcccc agggacagac gatgtcggtc ggcgttctcg atccgaccga  14460
catcacctat gcggctgccc agggtgccca gctccaggct ggcgtggtat cggccagcga  14520
caccgtgatc cgtaacagcc cggtcgctcg cgagcagctg gcgaacctgc cgcagcgcct  14580
ggctcagccc gccatggtgc tgtgggagcg tggcagcgaa tccctggtct atgtcgtcca  14640
ggacggcgac tctaccctgg cggttcgtct gcgcggtggc gtctatgggc cgggccaaat  14700
ggagaacatc agccaggtta cagaggtgac gatggaaagt atcgacgacg ggctcgccct  14760
gggccgttac aggagggttc gctaatggcc aatcgcatcg agctggaact ggtggaccgc  14820
gaggtccagg agcgcctggc ggcgctctac gcggcagtaa ccgacactct gccgctgatg  14880
cgcggcatcg ctgctgagct gctggccgag acggagtttg cattcatgga cgaggggccg  14940
ggatggcccc agttgagccc cgttaccgtt gcagcgcgag cggcgaaggg gcgcggcgcg  15000
catccgattc tccaggtcac caacgccctg gcgcgctcga tcacaacccg cgccgaccgt  15060
gaccaggcgc agatcggctc caatctgacc tacgcagcta tccagcagct gggcggccag  15120
gctggacgag gccgtaaggt gacaatccca gcgcgcccgt atctgccggt cctcagaagc  15180
ggccagctca agccaagcgc ccgcgatgcg gtcctggacc tcctcctggc tgttctgtcc  15240
cagggtcgct agagggaatg cattcggata agcggcacat tgtgcctatt gtgcattagg  15300
cacaatgtgc ctaatatggc gtcatgccag ccacaacggc gaggcgccaa gaaggatcga  15360
agccatgagc acccaacata cttacgaaga aatcgctgaa gacttccgtc tctggggcga  15420
gtacatggac cccaacgcag aaatgaccga agaggaattc caggccctct ccaccgatga  15480
gaaggtcgct atgcaggtcg aagcatttgg catggaaggt gagcaatgag caacacgatt  15540
tcagatcgca tcgtcgcgcg ctcggttatt gatgcggctc gattcatcca gtcgtgggaa  15600
```

-continued

```
gatgcagacc ccgacagcct gactgaaagc caggttctgg ccgccgctgg tttcgccgcc  15660
aggctccatg aggggctcca ggctaccgtc ctgcaacgac tggtggacga gtccaatcat  15720
gaagagtatc gcgagttcaa ggcatgggaa gaggcgctgc tcaacgcaga tgggcgggtc  15780
gcgagcagcc cgtttgccga ttggggatgg tggtatcgca tcgccaacgt gatgctggcc  15840
actgcctcgc agaacttagg cgtcacctgg ggaagccgcg tccatgggcg tttaatggct  15900
atttttcagg acaagttcaa gcagcggtat gaggaacagg catgagccga ccaacagtcg  15960
ttacggtgac ggaaaccccc aggaatccgg gaagctacga ggtcaacgta gagcgggatg  16020
gcaaaatggt cgttggccgg gcccgcgcgg gaagcgatcc cggcgcagct gcggcgaagg  16080
ccatgcagat ggccatggag tgggggagcc cgaactacgt cattctcggc agcaacaagg  16140
ttcttgcgtt cataccggag caactgcggg tgaaaatgtg aaacctgacg cctccagcca  16200
caatccagac ccgcgctacc tgcgcgggct gctcaagaaa gccggtatca gccagcggcg  16260
cgcagccgag ctgctcggcc tcagtgacag ggtgatgcgc tattacctga gcgaggatgt  16320
caaagagggc taccgtcccg cgccgtatac cgtccagttc gccctggagt gcctggcgag  16380
cgacccacca tctgcgtgat cacctgatcc gcccgcaaac gcgctacacg cgccgaaacg  16440
gggttagccg ctacctcgca tcagagtcgg tgcgttaacc ccgttagaac cccgttagaa  16500
atcgttccat cgccatccgc gtgccagggc ttagccagaa gacggcgccg gacggtttcc  16560
gcagtcgttg aacccccttca cgtaaccgcc gcgctcgacc gtcgccacca ttggcggcat  16620
gaagaagaac cgcctacacg ttgccatcgc cgcctgctcg ttccagctcc ccaagctgga  16680
ggacggcagc gcctggattc aagttacgcc tgccggtgag ttctggccca tggatgggcg  16740
ccctatggat gtgccgggct ggcggatcga tgccgccagt gccgccgcag tgatcgagcg  16800
cgcacggtcg cgcaagactc cgcccgtcct ggactacgag caccagaccc taaagaaaga  16860
gcagaacggc cagcccgcgc ccgctgccgg ccgtttcctg gacttcgaat ggcgcgaagg  16920
ctccggcctg tgggggcgtg tcgaatacac cgcccgcgcc gcgaagctga tcgaggacgg  16980
cgagtacctc tacttcagcc ccgtcttcag ctacgccccg gacggcacgg tcctctccat  17040
cctcatgggc gcaatgacaa atgaccccgc catcgacggt ctggagcctc tcgcacgccg  17100
agcggccgcg acctttggcc tctacaaccc cgacgaggaa acccctgtgg atgaactcct  17160
gaaagccatc atcgcggccc tgtcgctgaa agaaggcacg accgaggcag aggccattgc  17220
ggccctgacc gccctgaagc cggccctgga cgcccaagcg accaacctgg ccaagctgcg  17280
cgaaaccctc ggcctggccc aggacgcgga cgtcgagcag atcgccgccg ccaccgccca  17340
gctgaaggtc gccgcccccg gtaaccccga cccggcgaag tgggcgcccg ttgaagctgt  17400
cacccagctc cagggccagg tcgcggcgct gacctctcgc ctcaacggcg gcgagctgga  17460
cggcctgatc aacagcgcta tccaggaggg ccgactcatt ccgtccatgg agccctgggc  17520
gcgtgaatac ggcgccaagg acttggccgg cttgaagagc tacctgggcc aggccaagcc  17580
catcgccgcc ctgacccaac agcagagcgc cgggcgtacc tcggtgccta cctcggttga  17640
ccagctggac gaggccgccc tcgcggtttg ctcggccatg cagatcaagc ccgaggatta  17700
cctcaagacc ctgaaaggcc agtaaggagg cgctatgacc gccctgacca ccgaccgcaa  17760
caccccgctc caggacgccg aggtcatcgg cgtgccggta gcggccaacg tccaggtctt  17820
cgccggcgcc atcgtcgtgg cgaacgctac cgggttcgcc gtgggcggca gcaccgccac  17880
cggcctgacc tacctgggcc gcgctgagga atacgtggac aaccgcaatg gcgcggatgg  17940
cgccaaggtc gtccgtgtgc gccgcctgaa cgccttcaag tgggcgaacg acggcagcgt  18000
```

```
cacccaggcg cacctgatga aacccgccta catcgtggac gaccagaccg tcgccgccac  18060
ggacggcacc gaaacccgct ccccggccgg ccgcatcatc ggcgtcgaac cggacggcgt  18120
gtgggtggaa taacaggctc accaacggag aaccggacac atgctgatca acaagcagag  18180
tctcaacgcg gcattcgtcg cgatcaaaac catcttcaac aacgccttcg cggcggcccc  18240
caccacctgg cagaagatcg ccatggaagt gccgagcaac accagcagca acgattacaa  18300
gtggttgagc acctttccga agatgcgccg ctggatcggc gcgaaggtgg tcaagaacct  18360
gaaagcctac aagtacgttg tcgagaacga ggacttcgag gccaccgtcg aggtggaccg  18420
caacgacatc gaggacgacc aaatcggcat ctactcgccc caggcgaaga tggccggtta  18480
ctcggcggct cagctcccgg acgagctggt ctatgaagcg gtcaacggcg ccttcaccaa  18540
gccctgtttc gacggccagt atttcatcga cacggatcac cctgtcggtg atgcctcggt  18600
gagcaacaag ggcaccgctc cgctttccaa cgccagccag gcggcggcga aggcaggtta  18660
tggcgctgct cgcactgcga tgaagaagtt caaagacgag gaaggacgtt ccctcaacgt  18720
ctcccccaac gtgctcctgg tcggcccggc gctggaagac gtggcgaaga tgctgctcac  18780
caacccgaag ctcgcggaca acaccccgaa ccccctacgtc ggcactgctg agctggtagt  18840
ggacgggcgt atcgagtccg acaccgcctg gttcctgctg gacaccacca agccggtaaa  18900
accgttcatc ttccagccca ggaaacagcc ggaattcgtt tcccaggtca acctggattc  18960
ggatgacgtc ttcaacctgc gcaagctgaa gttcggcgcc gaagcccgcg ctgctgccgg  19020
ttacggcttc tggcagctgg cctatggctc caccggcact ggcgcataag gggcagctc  19080
atggcacgca aagccgcaac taccgccaag ccgaccgcca ggctggcccg ccaggcggcg  19140
ggcgatgaag cccagcagag cgtcgagggc atcttcgtgc gcagctatcc gccgaccttc  19200
cggcgtgctg gcttcgcgtt caccagcgaa ggaatcggaa tcgccctgtc cgccctgact  19260
gaggcgcagc tcaaggccat caaggaagag ccccagctgc gcgtcgagtc ctgcgagttc  19320
ttgccggacg acgtcggcgg cgagggtgag ccgtccgcgt cggacaacga cacccaggaa  19380
taacccaccc cagcagaggg accgcccctg gccacggatg gccacctatt cacaggagtt  19440
cgacatgagc gaccacaccc tggccatcag tcaactgacc atcgccgcgc agaacgccga  19500
gcacaacgct ccgatcatcg aagcccaggg cgacctcgcc caggccgagc tggatcgccg  19560
ggtcgctgcc gagtgccata gcgccatcga cgtcctggag caccaggagc agcaacagtg  19620
agctattgca cccaggccga cctggtcgag cagtacggcg aggcgtccat ccgccagctg  19680
agcgaccgcg tcaataaacc cgccacgacc atcgatccgg cggtcgtggc ccaggctatc  19740
gccgatgcgg acgcggagat cgatctccac ctgcacgccc gctaccagct gccgctggcc  19800
caggtacctg tggtgctgaa gcgcgtagcg tgcgtgctgg catttgccaa cctgcacacc  19860
caggtcaagg acgaccaccc cgcgatcctg gatgccgagc gcaagcggaa gctgctgagc  19920
ggtatttcct ccgggaagct cagcctggcc ctgaccagct ccggcacccc ggcgcccatt  19980
gccaacaccg ttcaaatcag ttcgcaacgc aacgatttcg gggcacctg gtgaccactg  20040
ccgagccgtt cgattacctg ttcctggaga cgctcctggt cgagcgcatc cgcgccgagg  20100
tgcccggcct tcaggacgtt tcgggcatcc ccgatctggc caccctcgac gaacagcgcc  20160
agggctcgcc ttgcgtctat gtcgtctacc tgggcgacga gatcggcacc ggggcgtcgc  20220
accagggcgg cagtcgggcg attcagacgg tcacccagca ctgggcagcc gtgctgacgt  20280
tgtactacgc cgacgcccag ggcgacggcc agggcgcccg gcgcgaagcc ggcccgctgc  20340
```

-continued

```
tcggccagct gctcaaggca ctgaccggct gggttcctga tcagggcgtc agcccgctgg  20400
cccgcagccc gcaggcttcg ccggtcagct acagcaacgg gttcttctat ttcccgctgg  20460
tattcaccgc caactttgtc ttcccgaggc tcaagtcatg gaaaccgtaa aagtcaccat  20520
caccgccgag aaacccaatc acacccatgc cggcaagccg gtggcgcagg gcgacgagat  20580
cgaagtcagt cgcgccgatg ccgagtttct gctgcgccgt caattgatca ccaagattcc  20640
cgccgagccc aaggccgacg agaaacgcga caagtaacgc gcaacatctg attcctacgg  20700
aggcctcaca tggcacagga aacgtatttc tacgggcaag gtgagattga cgccgcgcct  20760
atcgtcaacg gcgtcctcgg caaatggcgc tggattcagg atgtctcggc catgagcatc  20820
cagctcgcag tcgagaaggt cgagcacaag gaaagctaca gcggccagaa agccctggtc  20880
cgaagcttcc ccatcggcaa gaccgccacc gtcaacatca ccctacacag catcggcccg  20940
gacaacctgg cgcttaccct ctatggcaag gtcgtggcca aggcggcggg ctccgtgacg  21000
ggcgaggtac tccccgccga cctggtggct ggcgatgtga tccgattggc caatttcggc  21060
gtcagcgaac tggtcatcac cgacagcgcg agcagcccgg cgcccctcga cccgcagtat  21120
tacgccctgc gagccgatgg cgcctacggc gaggtccaac tgctgggtct gccgacgccg  21180
gccccgaccc agccgttcaa agcggcctat gagtacgccg ccaccaagca ggtgggcatg  21240
ttcaccgcgc cgcagccgac cgttgccctg cgctataagg gcatcaacct ggccgaaggc  21300
ggcgcgccgg tcatcgtcga gctgtacaag gtcgcgaccg acccgctcca ggagctggca  21360
ttgatcagcg acggcaacac cgtcgccggt atgcagatca gcggcggaat cctgctggac  21420
accagcaagc cggataccgg cgacctgggc cgcttcggcc gcattattca gctggggtga  21480
gtcatgaaga agccgaacga cacccccgtc gatgacagcc tggaagttct gttccccgac  21540
cgtcgtttga cggtcggggg cgaggacctg gttgtccgcg agctgacctt cgaagagcag  21600
ctcacccacc acgcggccct caaggccatt gccgaggcgt tcctccaggt gccgcgtgaa  21660
cacctcgaag gagtcgaggg cgcgaccatt gcgctggacg tgctgacgga gcactggaag  21720
ctcgttctgc cgttgattgc cgtgagctgt ggcaaggcgg atgactgggt ccgttcgctc  21780
cgtccaagcg acggtgagtc cctgatgctg gtctggtggg cagccaacca gggtttttttc  21840
gtccgccgcc tgtggcgccc gatagtaatg gctcaagccc tccaacaacg tggggtcgag  21900
tcttcgcctg cctcgtcgca gcaggacacc agcgcgacca gctcggccgc tacaccgagc  21960
gacagctaat gctgttcttc cgcgaagccg aggcagaaaa gggccgccag caagcccgcg  22020
agctgatggc ggtcaaccat ggcttcgccg gggctctgt agcgattgcc gcctatgatc  22080
agctcatgag taattgaacg tggccgacca agaccttgta ttagccctgc gcatccgcgc  22140
tgaccttcag cagggtgcgg accaggtcga ggaactgtcc gactcgatcc aagccgctgg  22200
cgaccatgcc agccaggctg gccgggagct gtccggtttg gggagacag ccgaccagca  22260
ggcggcccgg atcaaggcga tggtcgccgc ctccctgcaa cagcgggaag cgctggacgc  22320
gctggcggaa agttcggatc ggatgaacac cgccacgcgg gcagccacca gcggatggca  22380
ggaaagcgcc cgtgcgcaat cggcgtcgat gaatgcctac cacaacgccg agcgcgcccg  22440
cgaacagcag gttgcagccg agcaacgagc ggccgaggct gcggcgaaag ccaccgccga  22500
gttcgaccgg cagcaggccg agctgggcaa actgctcgcg gccatcgacc cggtcactcg  22560
cgagctggag aagctcgaca gcctccaggc gcgcctgaat gctgccaggg gtcgagggat  22620
cgacccggac gtctttacga cctacaacgc caagctccag gagcaacggg accgcctgct  22680
cggcacgtct gacgccatgg ccgtggccgg catttcggca ggtcagtacc gccaggccat  22740
```

```
gcggcagttg ccggcgcaga tcaccgacgt ggtcaccagc ctggccagcg ggatgccact  22800
gtggatggtt gccatccagc aaggcgggca gatcaaggac agtttcggtg gcgtcggcgc  22860
gacgtttcag gcgctgggcg atcaggtcaa atcgttcttc gggatcgcga gtaacgccag  22920
cgacggcctg gacgacatcg cccgaggggc ggacgctgcc gcagcgtcgg ccaacaacgc  22980
caagacggct atggtaggcc tcagcggagc aggtagcgcc tttatcgtca tcggcgcggc  23040
ggtggccgct gcgggcgtgg cgctggctct ggcgtatgag aaaggcagct cagaggcgga  23100
cgagctgaac aaggccatcg tcctgaccgg caactatgcc ggcactaccg ccgggcaact  23160
gtccgccatg gcggcgtcac tcgccagggc gaacggcact cagtatgagg ccgtggcggt  23220
actgtcggaa atcaccgcga ccggcaagtt cacggttgac cagatcgagc aggttgccac  23280
tacctccatc gcgatgcagg aagcgaccgg caaggctgtt tcggatacgg tcgccgagtt  23340
ctccaagctg gccgacgaac cggtcaaagc ctcgcaacag ctcaacgaga aatatcacta  23400
cctgaccgcc tcggtttacg agcagatagc cgccctcgat cagcaaggcg attcgctggg  23460
tgccgcccaa ctggccatgg acgcctatag ccaggcaatg gacgagcggg cgagccagat  23520
cgtcgagaac ctgggcaccc tggaaaccgc ttggaagacc gttgccgggg tggccaaggg  23580
cgcctgggac gaaatgctcg gcgtgggccg gacggagaca cccgaggaac gcctggagca  23640
actgaccaag gggcaggcct tccagccggg acgcgctgtg gccagcgggg ctgtcttcgg  23700
cccgttgggc tggttcaacg agctacgcaa ggcgtatcag cgcagctcga tgtcggacga  23760
cgagcgcggg aagcaattca ccgatgccct ccaggaaatc caggacgagg gcgagaaggc  23820
gcagaaggcg cgcctggatc gctacctgga ggacgaggca atacgcggcc agcagagcat  23880
ggacaagctg ctggagtcgg tgcgcaccaa caaggaaaag cgcgacaagc tcaacaggga  23940
gctggaccgg agcattgccg cgatccaggc ggctaacccg aacgacgaac gcctgcggcc  24000
ggaaaatatc gccgccgctc gcaaggccat cgatcagaag tacaaagacc cgaaaacccc  24060
gaaagggccg tctacgcccc tcgaccagtc cagcgtcacc gaggcgaaga accgcctgga  24120
ccagttgcaa accgatttca ggaacgccga gcagaagctc caggcgcagc agcgcgccgg  24180
cctgctgagc tatgcggact atgtcgcgca gcgcggcgaa ctgatcagcc agaacaagga  24240
ccaggtcacc gcagcctatg agggggaaat ccaggcgctg gaggcgctgc gcgacaaaag  24300
ttccaccacg gcggcccagc gcatcagcct ggaccagaag atcgccgagg ccaggaacaa  24360
catggtcaag gcgcagaaga aggccgacgc cgacctggaa gtcctccagc tcaacgaaca  24420
ggggcgcctg aagaaacaga cccaggcagt caaggcctac agcgatgcgc tccagcaaca  24480
acaggatgcg ctggccctcc agggccaacg tgccgccgct gccgtgggca tgggcgcgca  24540
acagcgccgc ctgttcgatc agcgtggcag ccttgacgac cgattcgcgc agcagcgcct  24600
ggacctggcg agccagtatg gtgacggctc gcgaggcatg agcctcgacg agtacaacga  24660
caagctcaag gcgctggaag cgaaccatgc cgcgatgacc cagcagctgc aacgcaacta  24720
cgccgacctt caggccgccc agggcaactg ggtcaacggg gcgacgtcgg cgttcgctga  24780
ctacatcgac tccgccagga acagtgcggg ccagacctac gaactgttta gtaacgcctt  24840
ctccggtctg gaggatgccg tcgttaattt cgtgatgact ggcaaggcgt cgctggatga  24900
cttcgtccgc accatgattg gcgacgtggc caggatggcg acccgccagt tgggtgcgtc  24960
tctgctttcc gggtttggcc tgggcggtgg caccgatggc ggcgcccagg ggctgacggt  25020
cggcgcctcg gctgtatccg cctcggccgg cgccctggcg actgctggcg gcacgctcct  25080
```

-continued

```
gagcggcgcc gccgctatcc aggccgctgc cgcctcgctg gccgccgcca atggtgtcag 25140
tggggtgacc ggcgctgcgg gagctgccgg ggccgctgga gtggctggtg gcgggagtgg 25200
ctggttgtct tcgatcacca gcattttcgg cttcgcgggt ggcggccagg tccagggacc 25260
aggcacaccg accagcgaca gcataccggc ctggctatcc aacaatgagg tcgtaatccg 25320
gtcggcatcc gccatgcagc cagggcttac tccgctgctg ctggacgtca accaacgcgg 25380
atgggcggcg ctacatgact gggcgggggc cgtccgccac gccaccgggg gcgtcgccgg 25440
cattcccgcg ccatccctac cacgcccaag catgggcgcc gctcagatac aggaaccgtc 25500
caagaacttc agcgcatcag tctccaacgc ggtccacctc catgctgttc aagaccccga 25560
ccagatggcg gccgacatgt gggccggcaa gggcggcgac cattacatcg tctggctgaa 25620
caagaaccgc caggccgtca agcaaatact cggaaactag gaattcatgg ctactgaaat 25680
cggcaccgcc acgaaccacc agaacctggt cgagcgcctc gtccagttcc tcaccgcgaa 25740
cccagacctg gtcgcggctg gccaggccta cgagaaggtt ttcgacaaca ccatccccgc 25800
gaccggaacg gccatcgccg tgcgccaggt gacactgcgc gccccaggcc tgggcggcac 25860
cgatagcatc tacatgggga ttcagagtta cggcgatacg gcgctggact actacaacct 25920
gcgcctgatg ggcggcacgg cgtttaatcc tggagcgatc ccgcccggtg gcgactactg 25980
gaccgcgttt gccaactaca gtccgcgggt ccaggcgctg ctgtggaacc agcccatgcc 26040
gtactggttc ttcgccaacg gccgacgctt ctgggtcgtc gtgaaagtct cgacgatcta 26100
cgagtcggcc ggcgccggct tcatcctgcc accctgtcca ccgtcgcagt acccgtaccc 26160
actcgctgta gtcgggtcgt atcgcgggga cgtcgctgtg cgctggtccg atgtgagtga 26220
ccggcaccga ggcatcagca gcccctacga gcgaagctgc tatctccgcg atcccgccgg 26280
gcgctggctc ggtttcactg tagacggagg ggctgccaac gagtccgact acaacaatcg 26340
gacgctcctc ccgctgggct gcggccgtta tgcgggcagc agtgacaccg tggtcaaaca 26400
actgcgggat tcattcggga agttcccgct caaggcgctg tcgttcgtca cccgcgaaac 26460
cgagggtcgc cgaaacctgg gcgacttcga cggcgctttc tacgtgccaa cgctcaactc 26520
cggcgccgag gacgtgattg tcgaggacgg agtggaccac gtcgttttcc aaaccgcttg 26580
gcgtagcggt aacccttggc tctacgcgat caggaaggac tgacatggcc tatttcacag 26640
gaacagctaa caacccgtcc gacctgctcg ccaaactgcg cgtccacgcc gagtcgctcg 26700
gctgggtcac cgaccgcgcc tcggcatcgg aatggctttg tcacaacgct gatgggtact 26760
ggtcattcaa tgccggagcc aatcagttcc agatggcggg caatacgggg ttcgataaca 26820
gcctggcgtg gaacgcgcag cccggtaact cggtgcagaa caacccttat tcgtcgaagg 26880
gaccgaccgt cgcacagctg agcggtgggc cgttcacgcg ctaccacctg tttgccacgg 26940
cggcctatct gcacctgcac gtcgagattg cggccggtca gttccggccg gtgatgattg 27000
gctcgctcaa caagcgcgga gtcgaataca gcggcggcca gtacgtatgc ggctccgtaa 27060
tctatcagtc gggccagatg ctgacatcga actggtcctg tcatccgttc gacggctatc 27120
acgttcgcta tagcgacggt ggttgcgtac tgcgtgtgga tggcctggat ggcggcccct 27180
cgcccgactg gctgccattc gactacgcga cgaacatccc ccggcgggtc atcgggccag 27240
gccgtggaaa ctacagaagt cagtaccatc ctgacgtcgg actgatcgac gccagcgcaa 27300
acgagctgaa cagctcgacc accactgtgc cgtgcgccat ctatgcgttc ggcgctcagc 27360
agcgctcgcg ctacgtgggc gaagtgccgg actttggcat atgcaacatg gccttcctcg 27420
cgcctggtga tccgcttgtc gtcggtagcg acacttggcg cgtatatccg ttgctccaac 27480
```

```
gcggaaccgc taccgacttc gacagcgcca gcgcctgggt cggctattgc ttccgggtgg  27540
tcgagtgatg gcgacgtttc cagggttcca ggtgccgaag cctgtggagg ggatcgttgc  27600
cggcatcacg ccgaatatcg acgccctgga gctgaaccag gacatcagcc ttgcagcggt  27660
cgcggcctcg acctgggccg gcgcctatgg ggcgcatcag ccggtagagg tgatccattc  27720
gacctaccag gctgtccacc aaagcgctct ggaagagaac tactacaacc gcctctggtt  27780
gattccgacc gcaatggaac tgggcaacgt cgtcagcacc cagatacgac cggcatcagt  27840
ctggaacgct tatttcagcc cgcgcatgct gaccgctatc gaccgcgaag ccgcagacgg  27900
cattacgctg tccggccagg cttcgccgcc gctgggtttt gccgccctgg aggaacgcac  27960
ctggacggtc agcattggca ccgacggccc gcccgtagtc aatgcccgaa tcatctggag  28020
gctccagggc gagccggacc tggccctggt catcactggc aatcgcatca tcgcctggac  28080
gttcgcgccg gactggggcg acagcatcgt cgaacgcctg agcgcatcga caaatatcct  28140
gcaaagcgaa tcggccgtga cccagcgccg agccatgcgc ctggcgccgc gccgagagtt  28200
cgaagcgaac atgtacgcgg tggatcgcga gcggcagttg ctggacatga cgctgttcgg  28260
ctggggtgcg cgcatttggg cgctgccgat ctggcctgat atccagctgc tccaccagcc  28320
gctggcggcc gggtcgctga gcattccgtg cgacacggcc ggcctcgact tccgcgacgg  28380
cggtctggcg atgctgcgcg gcgaggacgc ttttacttac gaggtcgtcg aggtcaagac  28440
ggtgaccgcc agcggcctgg acctggtccg gcccgtccag gccgcgtggg gaactggctc  28500
gcgactgtac ccagtgcgca ccgcgcagct gaccgaacag cccacgctga cccggctgac  28560
cgataccgcg cagtctgcgc gggtgtcgtt ccttgtgatg gaacccagca gttggcccga  28620
ggtgatgccg gcgacgatgt accgggggcg tcctgtcctg gaacagcgcc ccgacgaaag  28680
cgaagacctg acgtcgagct atcagcgcct gctgtccacc ctggataacg gcagcgccat  28740
tccccgcgtg accgacgtcg ccggcatggc gctgcccgtc atcggtcatc gctggatcgg  28800
catgggccga gccgaacggt cggcgttccg cagcctggtc tatgcgctac gcggccagca  28860
gaagccgctg tgggtgccga cccacgccga cgacctgacc ctggtcgcca ccgtctcgca  28920
gctgtccacc gcgctggacg tgcgcaatat cggctatgcc cgtttcgcca acggccggcc  28980
gggccgtcgc gatatccgca tcgagctata cgacggcacg gtctatcacc gccgcatcct  29040
caccagcaca gagctggacg ccgacaccga gcgcttggcc atcgatgccg ccctgggccg  29100
gctggtcgag cctggtgacg tggcgcgcat ttgtttcatg gcgctctgta gcgccgccac  29160
cgacgtggtc gagatcgagc acgtcactga tagcgagggc gtagcaactg ccgccctgac  29220
gttcaaaggg gttcgtgacg atgagtttta acagccgcga aagctcgctc gcggatgggc  29280
agccggtgcg gctgtaccag ttcagccgtg gagccatccg ctggagctac aacagcagcg  29340
accgggacat cacctaccag aaccagattt tccgcaccgt gccgggcggc atcactgaca  29400
acgggatcat ctgttccggc gatccgcagt ccgaccagtt cgtcatcacc gcgccggccg  29460
acctcgacgt cgcgctgctg tacaagaccc ggtcgccgag cggtgccatc gacttggtcg  29520
tctacgacat gcactacggc gacaccgagg cagcggtttc ctgggtgggc cagattggcg  29580
atgtggactg gccgaccgtg gacagctgcc gcataacgtg cgtgtcagaa gacgaactga  29640
tggaccagcc cggcttgatc gacacctact gccgcacctg cacggcagtc gttggcgacc  29700
atcgctgcaa ggtcaacctc gttccgtatc gcgtgacgct gacgccgcag agcatcagcg  29760
gctgggtgat ctccagcggc gtggtcgccg gctatgtcga tggctggttt accgggggct  29820
```

```
acgtcgagtg gcaagtggac ggcgacaact acgatagccg ctacatcgag cggcacgccg  29880
gacccgatct ttacatcctg ggcggcaccg agggcattcc ggcaggtggc caactgcggg  29940
tttatccagg ttgcgacggg ctcgcgcaga cctgcgacga caaattcagc aacctcccca  30000
acttcagggg gtttaacgcg atgcaaggca agtcgccatt cgatggcgac caggtctggt  30060
gaggtaggcc atggacccga tcacaatcaa tctcgtcatc ctggcggcgt cgttcatcct  30120
atccaaggtc ttggcgccga agccgcagaa gcccaagccg accgcctttg aagacatcga  30180
tttcccgcgc tgcgacgagg gtgacgaaca ggtcgccgtc ttcggtcagt gctggtcgaa  30240
gagctggatg gtgctgaccg tgggcaacta cagaacgaag gcgatcaaga ccaaagggag  30300
caagaaatga tcgttacggc tcagcacctg cataccgtgc cgacctggac cactcggcag  30360
ggctactgcc accggcaggc gcgggacttc ttcaagcgcc atggcctgga ttggatggcg  30420
ttcttacggg acggcatcga ggccgacgtg ctagtcgcga ccggcgacgc gctcgcgctc  30480
aagctggttg agcacgcatg ccaggaggta gccgatgggc gctaaaccga aggcacagac  30540
ggtcgggttc gagtactttt ttgacatcca tttcgccctg ggtaagaaga tcgacgaggt  30600
ctgtgcaatc cgggcgagcg gcaagaccgc atggaagggc tcgatcacca gtaacggcca  30660
ggttcgcatc aatgcgccgg acctcttcgg cgggaagaag ggcgaaggcg ggctcgacgg  30720
aacgcttgac gtgctgtttg gcgaggagga ccagggcgtc ctgccgcgcc tggcggcgat  30780
gctcggcggc ctggtaccgg cgttccgggg cgtcaccacg tgcttctatt ccggcctggt  30840
caccgccatg aacccctacc cgaagacctg ggagattctg cgccgaggcg gcaaccgcct  30900
gtgggacggc aacccctggt atcccgaaaa gcaatttatc tggctcgcgg acggtcagat  30960
caaggcgatg aatccggcgc atatcctcta tctcgtctac accggccggg acttccgggg  31020
gctggcccgc acgcggatgg acgaggcgag ctggcgggcc gctgccgaca agctgtatgc  31080
cgagggtttc gggctgtgct ttgaatggac caggtccgac acgttctcaa acttctgcga  31140
gacggtgaaa tcgcatatcg gcgccgaggt ttacccgaac cgacagaccg gacaaatcag  31200
catccgcctc ctgcgggacg actacagcgt tgcagacttg ccgctgttcg acgaggacag  31260
cggcctcctg gagatcaccc aggagaagac cggctcgacc tcgctcgcgc cgagccagct  31320
tatcgtcaag tacatcgacc agaccgacgg cgcgcagcgc caggtcatcg tcaacaacaa  31380
cgcggtcgcc gcttcgcagg ggcggcggtc gtccgaggaa gtcgagttcc tgggcgtgcc  31440
gactggcgag ctggccgggc gagtcgggga gcgggaaatg cgtctgaaga caaccggtct  31500
gaagcgctat aaaggcgtat tcgaccgccg cgcccgtagc ctgaaccctg gccagccgtt  31560
ccgcatccgt tcgacccggc gcggcatccc tgaaaccgtc gtccgggtcg gccggatcga  31620
ggacaacttc ctcggcgacg gcaagatcac cctgaccgtc gtccaggacc agttcaatct  31680
gccggcgact accggcgtgg caccaccgcc accaggctgg accccgcccg accggacgcc  31740
tcgggcggtc accgtgcggc gtctgatcga ggcgccatat cgcgaactgg ccggcgtgat  31800
cgatccggcg aatctccagc tcctggacgt gtccgcctcg tatcttgccg ccttggccga  31860
ggcgccgacg agcctgtcgc agagctacac cttgaccgac cgcgtcggca gttctggcgc  31920
gttcgttgat cgcggaaccg gcgactggtg cccgaccgga ctactcgccg ccgagctgcc  31980
gctggcggcc ggcccgaacg tcgtcacgtt gacgaacgcc acccggctgg aggacgtcac  32040
tgtcggccag gccgctgtgg tggacgacga gatagtccgg gtcgatgccg tcaactatgc  32100
cagtggcacc gtcaccctgg cgcgcggctg cgccgatacc gtgccggcca agcacttggc  32160
cggggctcgg gtctggttct acgacacgtt cgaagcggtg gacgagacgg tatacagcca  32220
```

```
gggcgtgacg ctccaggccc ggctgctgac caacaccagc gagggccagc tcgccccggc  32280
gctggccgcc accgacagcc tcactctgac cgggcgccag ggcaagccgt atccgcccgg  32340
ccagttccga atcaacggca gcgcgtaccc gacgaaggtc tacggagcgc tgtcggtgag  32400
ctgggcgatg cgcgaccgca tcggccaggc cgaccagttg atcgatacca ctgtcggcaa  32460
catcgggccc gaagatgggg cgacggtgac gctccaggtc tacagcggca cgacgctgaa  32520
gcgcacctat gccggcctca catccagtaa ctggtcctat ccgctggccg aagacgtcgc  32580
tgacggcctg ctccaggacg tgcgcctggt cctgcgcagc gtccgcgacg gcatccaatc  32640
ctggcagcaa cacgacatca ccatcgaacg acacggcctg ggcttccgct tgggcgaaga  32700
ccttggaggc gtttccgcat gactctctat atggggccta acaccggcct gctgatcaac  32760
ggcttgccgg gagaagggca ttacagcgat ctgattcgga tgtggcgctg ggatgacttt  32820
ctgaggcagc cggtcgtcaa ggggcgcgtc gccgcgctcc cgaccagcgg ccaggccgag  32880
ggggacacgt acattttcac tggctccggc tccaatcaga accgcctggc gcgctggtgg  32940
gcaacgggcg ccaccacggc aatttgggag tacatgccgc cacggctggg ctggcgtgtc  33000
caggtcgcaa acgagacgac gccgagcggc caggtcaaga cctacgagta ttccggcacg  33060
gcgtgggtcg agctggtggg cggtatgtcg gacgcgccca gcgacggcag caactacgca  33120
cgcaacaacg ggacgtgggg gaagctggga accgctgccg gagcagacct caacggcatg  33180
ccgttcctca atctgatgcc cgatagcggg cggtacgcag gcagtatcaa cccgctaatc  33240
ctgcgattca ctgaggcttt ttccagtacg ttcctgacgc catggaatgg cgcgtcaatc  33300
gctgacggcg gaaagtacat ctacgacaac accacaaacg gcgggacggc tggcaatctg  33360
aatcaacgtg tccaggactt actggtggcg atggggcggt ccagtggcag cttggcgcgc  33420
tatggcgtgg agttctatac cgctgtgctg accgctggcc ccaacgcaac gaccggctct  33480
acgggcgccg acggcacgac ccgttatctc cagatgacga actcgtcgag ggcgctcttc  33540
atcgccaacg gctggtgtac tgcggttctt tggatacgcg cggaggccgg atcgcttcac  33600
ttcatgccgg caacggcccc gacgactgac tacaagatat ggctgaatgg tgcgcctgta  33660
ctgccggggc aggtgctgac ccccggccgat ggatggaagc acgtcaggat ttccaaaaag  33720
agcgcgcagg gctacgacaa cggcttcccg ttcctctata tgtcgctggg cgccagtgca  33780
gctatggcct gtccggcatt cttcggcggc ctggtcgatc ccggcatcca cgtcgcgcct  33840
attgcaaccg tcaactcaca gagcgcatga caatgacgaa acgagttcta ttgaaaggcg  33900
agttcttcgc agagtgggcc ggctcgctgg acgaggccgc cgcactcgct ggcgtcccgg  33960
tcggcgacct ggcgttccat cccgacgacc tcctggccga agtccaggag ttacgccgcc  34020
aggcctatcg caccgagtcc gacccgctgc gcctggaggc cgagtttgac gccatagccg  34080
ctggcaccga gccggacctg gaggcatggg tcgcggccgt gcaggcgatc aaagaacgct  34140
atccgctccc ccagtcctaa gcgttttgat aattgtgacc aacgtcgcct ttttgctacg  34200
gtccctagct gatgtgcgga gtagataggg aagttggtat ggacgaggtg cttagacgga  34260
ggctgcgggc ggagctgctg gaggtggggt ttctcaacca gtgctgcctt gatctgatgg  34320
atgcgatgga ggccgagttc agcctcaccg aggaccagcg cgaatgcatc gagcagctcg  34380
gccgattcct gcgggagggc atcggcaagc tgaccgctct gtctgagcgg gtagccgatg  34440
gcgatatcgt cgtgctgtgc tgatcttttg aaattctttt gccgctggcg aaacggttag  34500
ggcgcgtcat ttattgcgca aatccgcgcc aaatttcgcg cccggtacag gcc         34553
```